United States Patent
Iezzi et al.

(10) Patent No.: US 10,486,140 B2
(45) Date of Patent: Nov. 26, 2019

(54) CATALYTIC COMPOSITION AND PROCESS FOR THE DEHYDROGENATION OF BUTENES OR MIXTURES OF BUTANES AND BUTENES TO GIVE 1,3-BUTADIENE

(71) Applicant: versalis S.p.A., San Donato Milanese (MI) (IT)

(72) Inventors: Rodolfo Iezzi, San Donato Milanese (IT); Giulio Manzini, San Giuliano Milanese (IT); Paolo Pollesel, San Donato Milanese (IT); Alessandro Del Seppia, Porto Mantovano (IT)

(73) Assignee: versalis S.p.A., San Donato Milanese (MI) (IT)

( * ) Notice: Subject to any disclaimer, the term of this patent is extended or adjusted under 35 U.S.C. 154(b) by 0 days.

(21) Appl. No.: 15/783,097

(22) Filed: Oct. 13, 2017

(65) Prior Publication Data
US 2018/0043338 A1    Feb. 15, 2018

Related U.S. Application Data

(62) Division of application No. 14/363,153, filed as application No. PCT/IB2012/057690 on Dec. 24, 2012.

(30) Foreign Application Priority Data

Dec. 28, 2011 (IT) ............... MI2011A2403

(51) Int. Cl.
*B01J 23/62* (2006.01)
*B01J 21/12* (2006.01)
(Continued)

(52) U.S. Cl.
CPC ............. *B01J 23/626* (2013.01); *B01J 21/12* (2013.01); *B01J 23/58* (2013.01); *B01J 23/62* (2013.01);
(Continued)

(58) Field of Classification Search
CPC . B01J 23/626; B01J 21/12; B01J 23/58; B01J 23/62; B01J 23/624; B01J 37/0045; C07C 5/3332; C07C 5/3335; C07C 5/3337
See application file for complete search history.

(56) References Cited

U.S. PATENT DOCUMENTS

| | | |
|---|---|---|
| 4,677,237 A | 6/1987 | Imai et al. |
| 5,677,237 A | 10/1997 | Tsai |

(Continued)

FOREIGN PATENT DOCUMENTS

| | | |
|---|---|---|
| EP | 0637578 | 2/1995 |
| WO | 2005/063658 | 7/2005 |

OTHER PUBLICATIONS

International Search Report and Written Opinion dated Jun. 26, 2013 in PCT/IB2012/057690.
(Continued)

*Primary Examiner* — James A Fiorito
(74) *Attorney, Agent, or Firm* — Oblon, McClelland, Maier & Neustadt, L.L.P.

(57) ABSTRACT

The present invention relates to a dehydrogenation process starting from reagents selected from single butenes, or mixtures thereof, or mixtures of butenes with butanes, to give 1-3 butadiene using catalytic composition of microspheroidal alumina and an active component containing a mixture comprising Gallium and/or Gallium oxides, Tin and/or Tin oxides, a quantity ranging from 1 ppm to 500 ppm with respect to the total weight of the catalytic composition of platinum and/or platinum oxides, and oxides of alkaline and/or alkaline earth metals.

22 Claims, 1 Drawing Sheet

(51) Int. Cl.
*B01J 23/58* (2006.01)
*B01J 37/00* (2006.01)
*C07C 5/333* (2006.01)
*B01J 21/04* (2006.01)

(52) U.S. Cl.
CPC ......... *B01J 23/624* (2013.01); *B01J 37/0045* (2013.01); *C07C 5/3332* (2013.01); *C07C 5/3335* (2013.01); *C07C 5/3337* (2013.01); *B01J 21/04* (2013.01); *C07C 2521/04* (2013.01); *C07C 2521/08* (2013.01); *C07C 2521/12* (2013.01); *C07C 2523/02* (2013.01); *C07C 2523/04* (2013.01); *C07C 2523/08* (2013.01); *C07C 2523/14* (2013.01); *C07C 2523/42* (2013.01); *C07C 2523/62* (2013.01); *C07C 2523/63* (2013.01)

(56) References Cited

U.S. PATENT DOCUMENTS

| | | |
|---|---|---|
| 7,473,668 B2 | 1/2009 | Bartolini et al. |
| 2003/0191351 A1 | 10/2003 | Voskoboynikov et al. |
| 2003/0202934 A1 | 10/2003 | Voskoboynikov et al. |
| 2005/0033101 A1 | 2/2005 | Voskoboynikov et al. |
| 2010/0168493 A1 | 7/2010 | Le Peltier et al. |
| 2010/0236985 A1 | 9/2010 | Luo |

OTHER PUBLICATIONS

Search Report as received in the corresponding European Patent Application 17162823.3-1371 dated Apr. 28, 2017.

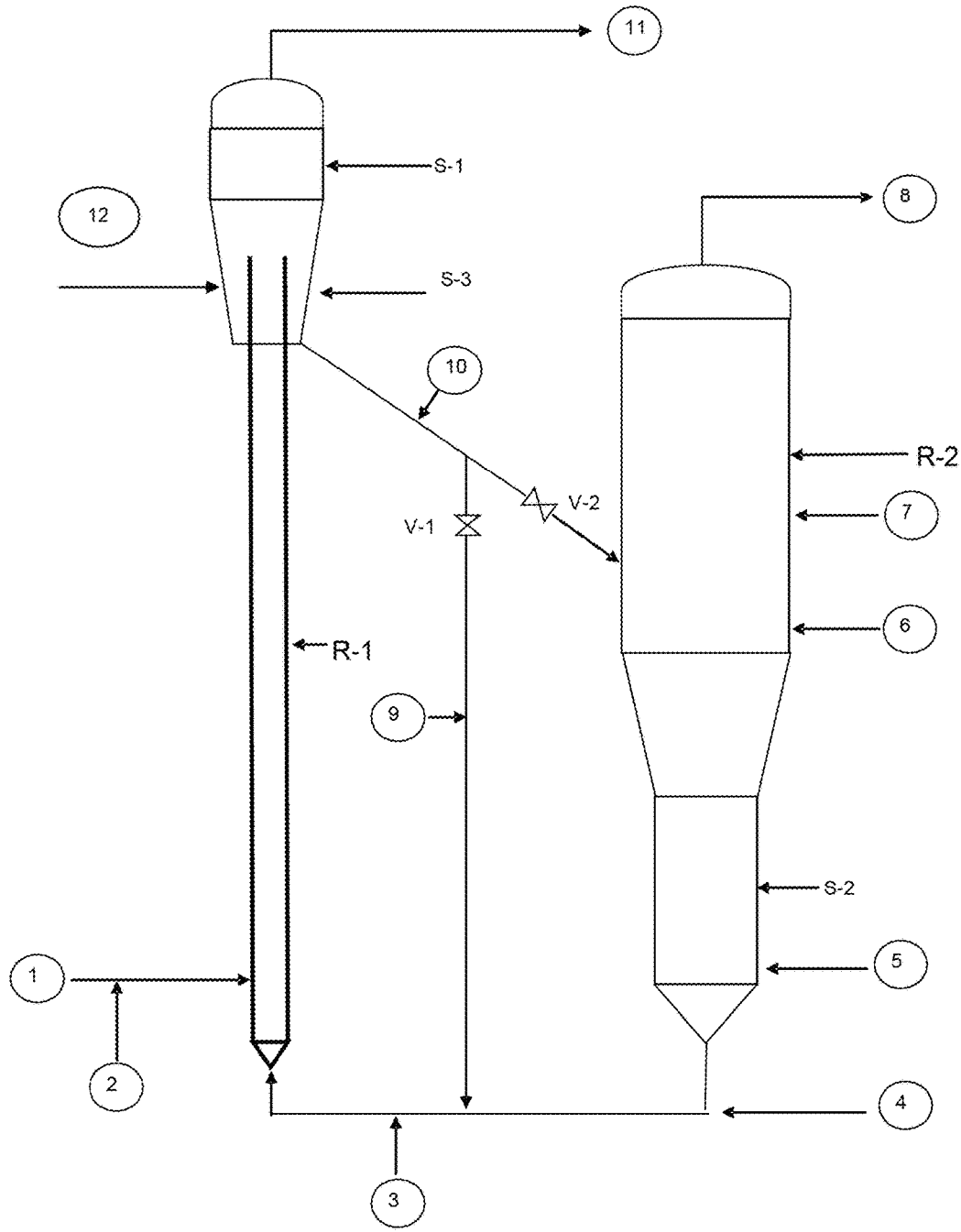

CATALYTIC COMPOSITION AND PROCESS FOR THE DEHYDROGENATION OF BUTENES OR MIXTURES OF BUTANES AND BUTENES TO GIVE 1,3-BUTADIENE

CROSS-REFERENCE TO RELATED APPLICATIONS

This application is a divisional of U.S. application Ser. No. 14/363,153 filed Jun. 5, 2014, which is pending, and which is a National Stage of PCT/IB2012/057690 filed Dec. 24, 2012, and claims the benefit of Italian application MI2011A 002403 filed Dec. 28, 2011.

FIELD OF THE INVENTION

The present invention relates to a catalytic composition and a process wherein said composition is used for the production of 1,3-butadiene starting from single butenes, or mixtures thereof, or mixtures of butanes and butenes.

DISCUSSION OF THE BACKGROUND

In the state of the art, the product 1,3-butadiene is prevalently provided by Steam Cracking processes from which it is selectively extracted from streams containing $C_4$ products or by the dehydrogenation of $C_4$ olefins and $C_4$ paraffins. With respect to the dehydrogenation, the technologies in use are the "Catadiene" process of CB&I Lummus technology, and the "OXO-D Process" developed by Petro-Tex (currently Texas Petrochemicals). Both of these processes are described in *Perp Report* Nexant Chem Systems Butadiene/Butylenes 09/10-5.

The "Catadiene" technology operates on a fixed adiabatic bed and under vacuum. As the catalyst must be frequently regenerated (the cycles last for less than an hour), more reactors are necessary for production continuity. The catalyst used is an extruded product based on chromium oxide and alumina.

The critical aspects linked to the Catadiene technology are described hereunder. The residual hexavalent Chromium, which therefore remains on the catalyst, is toxic and consequently has a significant environmental impact. The reaction takes place in the same reactor in which the catalyst is regenerated by air, thus creating conditions for a potential risk due to the mixing of air with hydrocarbon, in the case of a breakdown in the programming sequence of the large motorized valves for intercepting the streams between dehydrogenation, stripping, regeneration, stripping.

The ovens in which the feedstock is preheated, before being introduced into the catalytic bed, are sources of gaseous pollutants in particular NOx. As reactors for regeneration and stripping are required in addition to the reaction, the reaction volumes are high with significant investments.

The "OXO-D" technology operates with a fixed bed reactor in which the oxidative dehydrogenation of butenes is carried out, which are fed to the reactor mixed with vapour and air. This process operates without regeneration of the catalyst. There are essentially two critical aspects of the "OXO-D" technology.

The presence of oxygen imposes a severe section for the purification of 1,3-butadiene from oxygen, the latter being critical for the polymerization of 1,3-butadiene. The selectivity to useful product suffers from the presence of oxygen which favours the formation of combustion products consequently requiring that the OXO-D process operates through campaigns when there is a significant difference in price of 1,3-butadiene and that of butenes.

Various patents and patent applications are known, which describe catalytic compositions based on gallium, tin, platinum and alkaline or alkaline earth metals that the Applicant has listed hereunder:

US 2010168493 discloses:
a multi-metallic catalyst based on noble metals for dehydrogenation reactions starting from hydrocarbons, preferably light paraffins such as butanes and iso-butanes, or pentanes and iso-pentanes.
the use of the catalyst described in a dehydrogenation process of light paraffins (C4-C5) recovered after the extraction of unsaturated compounds from fractions coming from steam-cracking or catalytic-cracking.

The multi-metallic catalyst described in US 2010168493 comprises a noble metal M selected from Pt, Pd, Rh, Ir, at least one promoter X1 selected from Sn, Ge, Pb, possibly at least one promoter X2 selected from Ga, Ir and Tl, an alkaline or alkaline earth metal, supported on a substrate selected from Mg oxides, Ti oxides, Zr oxides, alumina, silica and mixtures thereof (silico-aluminates), wherein the atomic ratio X1/M ranges from 0.3 to 8, wherein the ratio $H_{ir}/M$ is higher than 0.4 and the bimetallic index BMI is higher than 108. The quantity of noble metal ranges from 0.01% wt. to 10% wt.

US 2005033101 discloses:
a catalytic composition containing a noble metal, an alkaline or alkaline earth metal, a compound selected from Sn, Ge, Pb, In, Ga, Tl or mixtures thereof;
a catalytic composition containing a noble metal (Pt), an alkaline or alkaline earth metal present as both metal and oxide, a third component selected from Sn as both metal and oxide, Ge, Pb, In, Ga, Tl and mixtures thereof, supported on a carrier having a surface area lower than 120 $m^2/g$ combined with a bulk apparent density higher than 0.5 $g/cm^3$;
a process comprising a catalytic dehydrogenation step in a fluid or mobile bed starting from hydrocarbons such as paraffins and $C_2$-$C_{30}$ olefins, in particular butanes, which generates a stream rich in hydrogen in vapour phase, a separation step which generates a liquid stream rich in hydrocarbons which is further separated according to a fractionation scheme.

According to US 2005033101, the carrier of the catalyst is alumina and it is essential for it to have a surface area lower than 120 $m^2/g$ combined with a bulk apparent density higher than 0.5 $g/cm^3$. It is also essential for the molar ratio of the alkaline or alkaline earth metal on the third component to be higher than 16. Finally, the quantity of Pt ranges from 0.01% wt. to 5% wt with respect to the final composition. The alkaline metal is present as both metal and oxide and ranges from 0.9% wt. to 1.1% wt with respect to the final composition. The third component ranges from 0.01% wt. to 10% wt with respect to the final composition. Sn is present as both metal and oxide.

EP 1492620 discloses:
a catalytic composition containing a first component selected from noble metals (Pt) or mixtures thereof, a second component ranging from 0.9% wt. to 1.1% wt with respect to the total weight of the final composition selected from alkaline or alkaline earth metals, a third component selected from Sn, Ge, Pb, In, Ga, Tl and mixtures thereof, supported on alumina having a surface area ranging from 50 to 120 $m^2/g$ combined with a bulk apparent density higher than 0.5 $g/cm^3$, wherein the molar ratio of the first component on the third component ranges from 1.5 to 1.7;

a catalytic composition comprising Pt, K in a quantity ranging from 0.9% wt. to 1.1% wt with respect to the total weight of the composition, a third component selected from Sn, Ge, Pb, In, Ga, Tl and mixtures thereof, supported on alumina (theta-alumina) having a surface area ranging from 50 to 120 m$^2$/g combined with a bulk apparent density higher than 0.6 g/cm$^3$, wherein the molar ratio of the Pt on the third component ranges from 1.5 to 1.7;

a process comprising a dehydrogenation step in a fluid or mobile bed wherein the hydrocarbon, preferably paraffins or C$_2$-C$_{30}$ olefins, is put in contact with the above catalyst, said step generating a stream rich in hydrogen in vapour phase, a separation step which generates a stream rich in liquid hydrocarbons which is further separated according to a fractionation scheme. The non-reacted hydrocarbons can be recirculated to the dehydrogenation step.

According to EP 1492620, the carrier of the catalyst is alumina and it is essential for it to have a surface area ranging from 50 to 120 m$^2$/g combined with a bulk apparent density higher than 0.5 g/cm$^3$. The quantity of noble metal ranges from 0.01% wt. to 5% wt with respect to the final composition (0.01% wt. is equivalent to 100 ppm by weight). The alkaline metal is present as both metal and oxide and varies from 0.9% wt. to 1.1% wt. with respect to the final composition. The third component ranges from 0.01% wt. to 10% wt with respect to the final composition. The Sn is present as both metal and oxide.

KR 0142305 describes a catalytic composition for the dehydrogenation of paraffins which comprises from 0.1% wt. to 1.5% wt. of Pt, from 0.05% wt. to 1% wt. of tin, from 0.05% wt. to 1% wt. of Ga and from 0.5% wt to 5% wt. of an alkaline metal on gamma-alumina.

U.S. Pat. No. 4,914,075 discloses:
a catalytic composition containing a first component selected from noble metals (Pt), a second component selected from alkaline or alkaline earth metals present as both metal and oxide, a third component selected from Sn as both metal and oxide, Ge, Pb, In, Ga, Tl and mixtures thereof, supported on alumina having a surface area lower than 120 m$^2$/g combined with a bulk apparent density higher than 0.5 g/cm$^3$;

a process comprising a catalytic dehydrogenation step in a fluid or mobile bed starting from hydrocarbons such as paraffins and C$_2$-C$_{30}$ olefins, in particular butanes, which generates a stream rich in hydrogen in vapour phase, a separation step of the stream rich in hydrogen which generates a stream rich in liquid hydrocarbons which is further separated according to a fractionation scheme.

According to U.S. Pat. No. 4,914,075, the carrier of the catalyst is alumina and it is essential for it to have a surface area lower than 120 m$^2$/g combined with a bulk apparent density higher than 0.5 g/cm3. The quantity of noble metal ranges from 0.01% wt. to 5% wt with respect to the final composition. The alkaline metal is present as both metal and oxide and varies from 0.01% wt. to 10% wt. with respect to the final composition. The third component ranges from 0.01% wt. to 10% wt with respect to the final composition. The Sn is present as both metal and oxide.

U.S. Pat. No. 7,235,706 discloses:
a catalytic system containing gallium or gallium compounds (Ga$_2$O$_3$) in a quantity ranging from 0.1 to 33.6% wt., platinum in a quantity ranging from 1 to 99 ppm, oxides of alkaline or alkaline earth metals in a quantity ranging from 0% wt. to 5% wt. on alumina modified with silica, the silica being present in a quantity ranging from 0.08% wt. to 3% wt.;

a process for converting C$_2$-C$_5$ paraffins to C$_2$-C$_5$ olefins comprising a dehydrogenation step and a regeneration step of the catalyst.

WO 2010107591 discloses:
a catalytic composition comprising a first component selected from Sn, Ga, Ge, Pb, In, Tl and their compounds among which the oxides (they are all alternative to each other), a second component selected from noble metals, from 0 to 2% wt. of an alkaline or earth alkaline metal also in oxide form, a carrier based on alumina or alumina modified with silica;

a catalytic composition comprising 0.25-5% wt. of a first component selected from Sn, Ga, Ge, Pb, In, Tl and their compounds among which the oxides (preferably Ga), from 5 ppm to 0.05% wt. of a second component selected from noble metals, from 0 to 2% wt. of an alkaline or earth alkaline metal also in oxide form, a carrier based on alumina or alumina modified with silica;

a catalytic dehydrogenation process of butanes to butylene with a regeneration step of the catalyst; the reactor can be a fast-riser.

U.S. Pat. No. 6,281,160 discloses:
a catalytic composition comprising at least one carrier, at least one metal selected from group VIII (Pt) of the periodic table, at least one element M selected from Ge, Sn, Pb, Re, Ga, In and Tl, and also a metal selected from alkaline or earth alkaline metals; the carrier is an oxide among which alumina, silica alone or in a mixture;

a dehydrogenation process starting from butanes to the corresponding olefins which uses the catalyst claimed.

The quantity of noble metals ranges from 0.1% wt. to 10% wt. The quantity of M ranges from 0.01% wt. to 10% wt. and the quantity of alkaline or earth alkaline metals ranges from 0.1% wt. to 3% wt.

U.S. Pat. No. 6,187,985 discloses:
a catalytic composition comprising at least one carrier, at least one metal selected from group VIII (Pt) of the periodic table, at least one element M selected from Ge, Sn, Pb, Re, Ga, In and Tl, and also a metal selected from alkaline or earth alkaline metals; the carrier is an oxide among which alumina, silica alone or in a mixture;

use of the catalyst in dehydrogenation processes of C$_5$ paraffins which are recovered after extracting unsaturated compounds from the C$_5$ fractions coming from steam-cracking or catalytic cracking.

The quantity of noble metals ranges from 0.1% wt. to 10% wt, the quantity of M ranges from 0.01% wt. to 10% wt. and finally, the quantity of alkaline or earth alkaline metals ranges from 0.1% wt. to 3% wt.

A further critical aspect is linked to dehydrogenation catalysts containing significant quantities of platinum to be treated with chlorinated compounds or chloro-gas, or in regeneration phase or after this, to favour re-dispersion of the platinum to restore its catalytic activity. The treatment with chlorinated compounds is followed by reduction treatment in which the catalyst comes into contact with hydrogen to reduce the platinum to the metallic state before the dehydrogenation reaction. The use of chlorinated compounds leads to the introduction into the atmosphere of acid gases in addition to being critical for the corrosion of the equipment.

SUMMARY OF THE INVENTION

The Applicant has now found an extremely active catalytic composition which is capable of operating with low contact times, comprising microspheroidal alumina, preferably modified with silica, and an active component containing a mixture comprising Gallium and/or Gallium oxides, Tin and/or Tin oxides, a quantity ranging from 1 ppm to 500 ppm with respect to the total weight of the catalytic composition of platinum and/or platinum oxides, and oxides of alkaline and/or alkaline earth metals.

The innovative idea is based on an extremely active, non-toxic catalytic composition, which, used in a reactor preferably of the fast-riser or fluid bed type, also exerts the function of thermal vector in the process, to compensate for the endothermic nature of the dehydrogenation reaction, and overcomes the critical aspects of current commercial technologies.

The continuous regeneration of the catalyst reduces the reaction volumes with the same productivity, and at the same time avoids problems of safety associated with the air-hydrocarbon mixture, as the regeneration of the catalytic system is effected in an operative unit specifically dedicated to regeneration.

Further objectives and advantages of the present invention will appear more evident from the following description and enclosed FIGURES, provided for purely illustrative and non-limiting purposes.

BRIEF DESCRIPTION OF THE DRAWING

FIG. 1 illustrates a process scheme relating to an embodiment according to the present invention wherein (1) is the feeding to the process, (2) is the inert product, (3) is the hot catalyst, (4) is the carrier gas of the catalyst, (5) is nitrogen for stripping, (6) is air, (7) is fuel gas, (8) are the combustion effluents, (9) the recycling of the partially exhausted catalyst to the reaction section, (10) is the partially exhausted catalyst, (11) is the effluent of the reactor, (12) is the nitrogen for stripping, (R-1) is the "Fast Riser" dehydrogenation section, (R-2) is the regenerator for regenerating the catalyst, (S-1) is the separation section of the catalyst, (S-2) is the stripping section of the regenerator, (S-3) is the stripping section of the Fast Riser, V-1 and V-2 are two valves.

DETAILED DESCRIPTION

An object of the present invention relates to an extremely active catalytic composition which is capable of operating with low contact times in a single dehydrogenation section having reduced dimensions.

Said catalytic composition comprises a microspheroidal alumina carrier and an active component containing a mixture comprising Gallium and/or Gallium oxides, Tin and/or Tin oxides, a quantity ranging from 1 ppm to 500 ppm with respect to the total weight of the catalytic composition of platinum and/or platinum oxides, and oxides of alkaline and/or alkaline earth metals. The alumina carrier is preferably modified with silica.

It is fundamental for the present invention that the platinum and/or platinum oxides be present in modest quantities in the catalytic composition, preferably from 1 ppm to 99 ppm by weight, even more preferably from 1 ppm to 50 ppm by weight. Excessively high quantities of platinum in the catalytic composition, in fact, make necessary for the catalyst, possibly regenerated, to be subjected to further treatment with chlorine-based dispersing agents to reduce sintering problems. For this purpose, the Applicant uses extremely low quantities of Pt and/or Pt oxides so that after regeneration, the catalytic composition can be immediately re-used without further treatment neither for re-dispersion nor for reduction. The absence of the re-dispersion phase avoids acid emissions into the atmosphere.

The gallium oxides are preferably selected from $Ga_2O_3$, $Ga_2O$ and mixtures thereof. The tin oxides are preferably selected from $SnO$, $SnO_2$ and mixtures thereof. The platinum oxides are preferably selected from $PtO$, $PtO_2$ and mixtures thereof. An oxide of alkaline metals is preferably $K_2O$.

A preferred catalytic composition comprises a mixture of gallium oxides, oxides of alkaline and/or alkaline earth metals, tin and a quantity of platinum lower than 250 ppm, supported on microspheroidal alumina modified with silica.

A further preferred catalytic composition comprises a mixture of $Ga_2O_3$, $K_2O$, $SnO$ and Platinum supported on microspheroidal alumina modified with silica.

The catalytic composition, object of the present invention, preferably contains a microspheroidal alumina carrier modified with silica, as it is particularly suitable if the reaction takes place in fluid bed reactors or in a Fast Riser reactor. The active part is deposited on the microspheres of alumina modified with silica, and can be modified with modest quantities of Platinum.

The quantity of Gallium and/or Gallium oxides preferably ranges from 0.1% by weight to 34% by weight, more preferably from 0.2% by weight to 3.8% by weight, with respect to the total weight of the catalytic composition.

The quantity of oxides of alkaline and/or alkaline earth metals preferably ranges from 0.05% by weight to 5% by weight, more preferably from 0.2% by weight to 3.8% by weight, with respect to the total weight of the catalytic composition.

The quantity of tin and/or tin oxides preferably ranges from 0.001% by weight to 1% by weight, more preferably from 0.05% by weight to 0.4% by weight, with respect to the total weight of the catalytic composition.

The concentration of platinum preferably ranges from 1 ppm to 500 ppm by weight, more preferably from 1 ppm to 99 ppm by weight, even more preferably from 1 to 50 ppm, with respect to the total weight of the catalytic composition.

The quantity of silica present in the carrier ranges from 0.05% by weight to 5% by weight, more preferably from 0.03% by weight to 3% by weight, with respect to the total weight of the catalytic composition, the remaining percentage being alumina. The surface area of the microspheroidal alumina is preferably lower than or equal to 150 $m^2/g$.

The concentration of $Ga_2O_3$ more preferably ranges from 0.1% by weight to 34% by weight, more preferably from 0.2% by weight to 3.8% by weight, with respect to the total weight of the catalytic composition. The quantity of $K_2O$ preferably ranges from 0.05% by weight to 5% by weight, more preferably from 0.1% by weight to 3% by weight, with respect to the total weight of the catalytic composition. The SnO preferably ranges from 0.001% by weight to 1% by weight, more preferably from 0.05% by weight to 0.4% by weight, with respect to the total weight of the catalytic composition. The quantity of platinum preferably ranges from 1 ppm to 500 ppm by weight, more preferably from 1 ppm to 99 ppm by weight, even more preferably from 1 ppm to 50 ppm, with respect to the total weight of the catalytic composition.

The catalytic composition, object of the present invention, is suitable for operating with fixed-bed and mobile-bed reactors.

The catalytic composition, object of the present invention, is obtained by means of a process which essentially consists of dispersing the precursors of the active principles on the microspheres of modified alumina. This dispersion treatment can consist of impregnating said carrier with a solution containing the precursors of the active principles, followed by drying and calcination; or by means of ionic absorption, followed by separation of the liquid and activation, or by surface adsorption of volatile species of the precursors, and possible calcination of the solid. Among those listed, the preferred procedures are: impregnation of the carrier with the volume of solution equal to that given by the pores (specific porosity of the carrier [cc/g] multiplied by the gr. of carrier to be impregnated) which corresponds to the amount of carrier to be treated. This impregnation procedure known as incipient wetness process. Or immersion of the carrier in a volume of solution, in excess with respect to that which corresponds to the pores, in which the precursors of the active ingredients are dissolved, followed by evaporation and subsequent calcination. The precursors of the active principles can be contemporaneously dispersed, in a single step, on the carrier, modified with silica, or in several steps:

in the first step, the carrier, preferably modified with silica, is impregnated with the solution containing a precursor of gallium and potassium, followed by drying and calcination; or the carrier, preferably modified with silica, is impregnated with the solution containing a precursor of gallium, potassium and tin, followed by drying and calcination;

in the second step, the calcined product coming from the first step is impregnated with the solution containing the precursor of platinum and tin, the impregnated product is dried and finally calcined; or the calcined product coming from the first step is impregnated with a precursor of platinum, the impregnated product is dried and finally calcined.

A further object of the present invention relates to a dehydrogenation process starting from reagents selected from single butenes, or mixtures thereof, or mixtures of butenes with butanes, to give 1-3 butadiene.

Said process comprises the following phases:

diluting said reagents with an inert product before feeding them to a dehydrogenation section;

dehydrogenating said reagents in said dehydrogenation section in the presence of the catalytic composition according to claims 1 to 18, thus producing a gaseous effluent containing 1-3 butadiene;

sending at least a part of the exhausted catalytic composition to a regenerator;

at least partially regenerating said catalytic composition, exhausted after the reaction, in the regenerator by feeding a stream containing an oxidant selected from air, air poor or rich in oxygen;

sending the regenerated catalytic composition back to the dehydrogenation section.

The part of the catalytic composition that is sent to the regenerator preferably ranges from 50% to 80% and consequently the part that is not regenerated ranges from 50% to 20%. The part of the catalytic composition that is not sent to the regenerator is recirculated directly to the dehydrogenation section.

The reaction device for dehydrogenation according to the present invention can be similar to that adopted in "Fluid Catalytic Cracking" (F.C.C.) processes, thus obtaining a reduction in the reaction volumes. A regenerator of the catalytic composition described and claimed in the present text is associated with the dehydrogenation section. The regeneration preferably provides combustion with air of the coke deposited on the catalyst during the dehydrogenation and forms combustion products. The dehydrogenation reaction and regeneration are effected in two separate apparatuses thus avoiding the formation of mixtures of hydrocarbon in air which is potentially risky. The catalytic composition is always recirculated between the reaction section and a regenerator and viceversa, using a carrier gas. The same carrier gas can be used for diluting the feedstock at the inlet of the reaction section. The inert product for diluting the feedstock can be selected from nitrogen, methane, or another fuel gas with a maximum hydrogen content equal to 1% by weight.

The inert product has the function of lowering the partial pressure of the reagents and products in order to increase the conversion and reduce the kinetics of parasite reactions so as to preserve the selectivity to the desired product. The carrier gas can be nitrogen, or methane or another fuel gas with a maximum hydrogen content equal to 1% by weight, which offer the advantage, with respect to nitrogen, of recovering the calorific value of the hydrogen without the need for cryogenic separation.

In the process, object of the present invention, the use of ovens for preheating the feedstock is not envisaged, thus reducing the formation and emission of NOx. The same catalytic composition described and claimed in the present text forms the thermal vector of the dehydrogenation reaction yielding the sensitive heat accumulated during the regeneration. The combustion of the coke present on the exhausted catalytic system generates heat entirely recovered for the dehydrogenation reaction and integrated with aliquots of fuel gas added in the regeneration device to be able to completely balance the endothermic dehydrogenation reaction. Natural gas or hydrogen or fuel gas obtained from a mixture of the two, can be used as fuel gas in the regeneration section.

Preferably the dehydrogenation section suitable for the present invention can be a fixed-bed reactor, a fluid-bed reactor or a mobile-bed reactor. Even more preferably, the reaction device is a "Fast Riser" reactor into whose base the feedstock to be dehydrogenated is charged. In the dehydrogenation section, the feedstock is mixed with the at least partially regenerated catalytic composition, described and claimed in the present text, which enters the base of the reactor. The feedstock is dehydrogenated in said reactor as the catalytic composition and feedstock advance in equicurrent, until they have passed through the whole reactor. The catalytic system is separated from the gaseous effluent at the head of the reactor, and is sent to the regeneration device. The catalytic composition, object of the present invention, can be entirely or partially sent to regeneration. The non-regenerated part is recycled directly to the reaction device. After regeneration, the catalytic composition is re-circulated to the reactor.

In the dehydrogenation section, it is preferable to operate at a temperature ranging from 450° C. a 700° C. The dehydrogenation pressure preferably ranges from 0.2 atm absolute to 2 atm. The ratio inert product/feedstock (v/v) ranges from 0 to 20, preferably from 1 to 9. The inert product for diluting the feedstock can be selected from nitrogen, methane, or another fuel gas with a hydrogen content equal to 1% by weight.

If the reactor is a Fast Riser, the residence time of the gas phase is less than a minute, and preferably ranges from 0.2 sec. to 5 sec.

The regeneration is preferably effected in a fluid bed at a temperature higher than the operating temperature of the reaction section, preferably higher than 700° C. The pressure in the regeneration section is slightly higher than atmospheric pressure. The residence time of the catalytic system during the regeneration ranges from 5 to 60 minutes, preferably from 20 to 40 minutes. During the regeneration, the hourly space velocity of the gas phase (GHSV in Nl/h air per litre of catalyst) ranges from 1,000 to 5,000 h$^{-1}$, preferably from 2,000 to 3,000 h$^{-1}$.

The regeneration of the catalytic system and combustion of the fuel can be effected with air, oxygen or any other fuel.

The advantages of a reactor-regenerator system, and particularly a Fast Riser reactor-regenerator, can be summarized as follows.

- reduction in the reaction volumes and consequent investment;
- the heat required for the reaction is transferred directly by the regenerated catalyst, there are no ovens for pre-heating the feedstock upstream of the reaction section, with the possibility of the formation of undesired combustion by-products;
- no specific treatment is necessary for reducing emissions of gaseous pollutants;
- the reaction and regeneration take place in physically separate areas and there can be no mixing of hydrocarbon streams with streams containing oxygen;
- the regeneration of the catalyst effected in a fluid bed prevents the formation of high-temperature points, due to the vigorous remixing of the bed, preventing thermal stress of the catalytic formulate;
- the functioning of the plant does not have to be interrupted for the substitution of the catalyst as aliquots are periodically discharged and replaced with equal amounts of fresh catalyst when the unit is operating.

Some non-limiting examples of the present invention are now provide hereunder.

Example 1

A microspheroidal pseudoboehmite modified with silica (1.2% by weight) is prepared, having a particle diameter ranging from 5 μm to 300 μm, by spray drying a solution of alumina hydrate and Ludox silica. A part of the pseudoboehmite is calcined at 450° C. for an hour and subsequently treated at 1140° C. for 4 hours. The calcined product has a specific surface of 70 m$^2$/g and a specific porosity of 0.2 cc/g. A sample of 3250 g of calcined product is impregnated, by means of the incipient wetness procedure, with an aqueous solution consisting of: 573 gr of a solution of gallium nitrate (titre 9.3% by weight of Ga), 131.8 gr of a solution of potassium nitrate (titre 6.86% by weight of K) and water until the volume of the solution is brought to 1040 cc. The impregnated product was dried at 120° C. for 4 hours and finally calcined according to the thermal profile: from room temperature to 460° C. in 533 minutes and an isotherm step of 180 minutes at 460° C. 3270 gr of the calcined product consisting of 2.15 by weight of Ga$_2$O$_3$ 0.33% by weight of K$_2$O, Al$_2$O$_3$ and SiC$_2$ for the remaining part, were impregnated with the incipient wetness procedure with an aqueous solution containing dissolved: 230 g of anhydrous citric acid, 33.343 g of a solution of tin tetrachloride (titre 7.52% by weight of Sn) and 1.335 g of solid ammonium tetrachloro-platinite (titre 52% by weight of Pt) and water until the volume of the solution had been brought to 1046 cc. The impregnated product was dried at 120° C. for 4 hours and finally calcined according to the thermal profile: from room temperature to 120° C. in 120 minutes, followed by an isotherm step at 120° C. for 120 minutes, then from 120° C. to 250° C. in 120 minutes, from 250° C. to 730° C. in 210 minutes, followed by an isotherm step at 730° C. for 90 minutes. The weight composition of the catalytic system proves to be: 2.15% by weight of Ga$_7$O$_3$, 0.33% by weight of K$_2$O, 212 ppm by weight of Pt, 766 ppm by weight of Sn, the remaining part being Al$_2$O$_3$ and SiO$_2$.

Example 2

A 3250 g sample of the same calcined boehmite as Example 1 was impregnated using the same procedure described in Example 1 with an aqueous solution containing, dissolved: 573 gr of a solution of gallium nitrate (titre 9.3% by weight of Ga), 131.8 gr of a solution of potassium nitrate (titre 6.86% by weight of K) and water until the volume of the solution was brought to 1040 cc. The impregnated product was dried and calcined under the same conditions described in Example 1. 3270 gr of the calcined product consisting of 2.15% by weight of Ga$_2$O$_3$, 0.33% by weight of K$_2$O, the remaining part being Al$_2$O$_3$ and SiO$_2$, were impregnated with the same procedure as Example 1, with a solution containing: 230 g of anhydrous citric acid, 1.3354 g of ammonium tetrachloro-platinite (titre 52% by weight of Pt), 65.337 g of a solution of tin tetrachloride (titre 7.52% by weight of Sn). The impregnated product was dried and calcined following the same procedure adopted for preparing the catalytic system described in Example 1. The weight chemical composition of the catalytic system is: 2.15% by weight of Ga$_2$O$_3$, 0.33% by weight of K$_2$O, 212 ppm by weight of Pt, 1500 ppm by weight of Sn, the remaining part being Al$_2$O$_3$ and SiO$_2$.

The catalytic systems prepared were tested for dehydrogenating mixtures of butenes in the co-presence of C$_4$ paraffins, prevalently n-Butane, in a circulating fluid-bed pilot plant equipped with a reactor and regenerator. The catalytic performances are indicated in Table 2, in which conversion (A) and selectivity (B) are calculated according to the following formulae:

$$\{[\Sigma(\Sigma butanes + \Sigma butenes)_{reactor\ inlet} - \Sigma(\Sigma butanes + \Sigma butenes)_{outlet\ reactor}]/\Sigma(\Sigma butanes + \Sigma butenes)_{reactor\ inlet}\}*100 \quad (A)$$

$$\{1,3 butadiene_{reactor\ outlet}/[\Sigma(\Sigma butanes + \Sigma butenes)_{reactor\ inlet} - \Sigma(\Sigma butanes + \Sigma butenes)_{reactor\ outlet}]\}*100 \quad (B)$$

The composition of the feedstocks treated in both Examples are indicated in Table 1.

TABLE 1

| Components | MIX 1 % by weight | MIX 2 % by weight |
|---|---|---|
| N2 | 2.288 | absent |
| CH4 | absent | absent |
|  | 0.001 | absent |
| CO2 | absent | absent |
| C2H6 | absent | absent |
| C2H4 | absent | absent |
| C2H2 | 0.083 | absent |
| C3H4 | 0.086 | absent |

TABLE 1-continued

| Components | MIX 1<br>% by weight | MIX 2<br>% by weight |
|---|---|---|
| C3H8 | 0.058 | absent |
| C3H6 | 0.018 | absent |
| n-C4H10 | 12.903 | 27.98 |
| iso-C4H10 | 3.563 | absent |
| iso-C4H8 | 0.690 | absent |
| 1-C4H8 | 52.381 | 13.21 |
| 2-C-C4H8 | 12.362 | 21.5 |
| 2-Trans C4H8 | 15.450 | 37.31 |
| 1-3 C4H6 (BTD) | 0.057 | absent |
| 1-2C4H6 | 0.000 | absent |
| C5H12 | 0.030 | absent |
| C5H10 | 0.030 | absent |
| C6H14 | 0.001 | absent |

TABLE 2

Catalytic Performances

| Ex. | Feed | Riser head T° C. | τ (sec) of reagents In Riser | Molar fract. hydroc. feed at react. inlet | Inert type for feed dilution | Operating. press (abs. atm) | Conv. (%) | Selectiv. % wt 1,3 butadiene |
|---|---|---|---|---|---|---|---|---|
| 1 | Mix 1 | 528 | 1 | 0.11 | Nitrogen | 2 | 17.2 | 88.6 |
| 1 | Mix 1 | 554 | 1 | 0.11 | Nitrogen | 2 | 19.9 | 87.7 |
| 1 | Mix 1 | 569 | 1 | 0.11 | Nitrogen | 2 | 21.8 | 85.3 |
| 1 | Mix 1 | 528 | 1 | 0.11 | Methane | 2 | 16 | 89.5 |
| 1 | Mix 1 | 554 | 1 | 0.11 | Methane | 2 | 19 | 87.5 |
| 1 | Mix 1 | 569 | 1 | 0.11 | Methane | 2 | 20.5 | 86.1 |
| 1 | Mix 2 | 530 | 1 | 0.11 | Nitrogen | 2 | 17 | 87.7 |
| 1 | Mix 2 | 550 | 1 | 0.11 | Nitrogen | 2 | 21 | 86 |
| 1 | Mix 2 | 570 | 1 | 0.11 | Nitrogen | 2 | 24 | 82 |
| 2 | Mix 2 | 530 | 1 | 0.11 | Nitrogen | 2 | 20 | 90 |
| 2 | Mix 2 | 550 | 1 | 0.11 | Nitrogen | 2 | 23 | 88 |
| 2 | Mix 2 | 570 | 1 | 0.11 | Nitrogen | 2 | 26 | 84 |

The invention claimed is:

1. A process of producing 1-3 butadiene, the process comprising:
   diluting a reagent selected from the group consisting of butane, a mixture of butenes, and a mixture of butenes and butanes with an inert product before feeding the diluted reagents to a dehydrogenation section;
   dehydrogenating said reagent in said dehydrogenation section in the presence of a catalytic composition which comprises microspheroidal alumina and an active component containing a mixture comprising
   at least one of gallium and Gallium oxides,
   at least one of tin and tin oxide,
   at least one of platinum and a platinum oxide in a quantity ranging from 1 ppm to 500 ppm with respect to the total weight of the catalytic composition, and
   at least one oxide of alkaline metal and an alkaline earth metals,
   thus producing a gaseous effluent comprising 1-3 butadiene and an exhausted catalytic composition;
   sending at least a part of the exhausted catalytic composition to a regenerator;
   at least partially regenerating said exhausted catalytic composition in the regenerator by feeding a stream comprising an oxidant selected from air, air poor in oxygen and rich in oxygen;
   sending the regenerated catalytic composition back to the dehydrogenation section, and
   wherein the dehydrogenation section comprises at least one Fast Riser reactor into whose base the reagents to be dehydrogenated is charged, the reagents are mixed with the at least partially regenerated catalytic composition, and the residence time of the gas phase in the Fast Riser ranges from 0.2 sec. to 5 sec.

2. The process according to claim 1, wherein in said catalytic composition the alumina is modified with silica.

3. The process according to claim 1, wherein said catalytic composition comprises gallium oxide, which is selected from the group consisting of $Ga_2O_3$, $Ga_2O$ and a mixture thereof.

4. The process according to claim 1, wherein said catalytic composition comprises tin oxide, which is selected from the group consisting of SnO, SnO, and a mixture thereof.

5. The process according to claim 1, wherein said catalytic composition comprises platinum oxide, which is selected from the group consisting of PtO, $PtO_2$ and a mixture thereof.

6. The process according to claim 1, wherein said catalytic composition comprises an oxide of an alkaline metal, which is $K_2O$.

7. The process according to claim 1, wherein the active component is a mixture comprising gallium oxide, an oxide of alkaline metal and/or an alkaline earth metal, tin and platinum in an amount less than 250 ppm, supported on microspheroidal alumina or on microspheroidal alumina modified with silica.

8. The process according to claim 1, wherein said catalytic composition comprises gallium, gallium oxide, or both in an amount of from 0.05% by weight to 34% by weight with respect to the total weight of the catalytic composition.

9. The process according to claim 1, wherein said catalytic composition comprises an oxide of an alkaline metal, an oxide of an alkaline earth metal or both in an amount of from 0.1% by weight to 5% by weight with respect to the total weight of the catalytic composition.

10. The process according to claim 8, wherein said catalytic composition comprises gallium, gallium oxide, or both in an amount of from 0.2% by weight to 3.8% by weight with respect to the total weight of the catalytic composition.

11. The process according to claim 9, wherein said catalytic composition comprises an oxide of an alkaline metal, an oxide of an alkaline earth metal, or both in an amount of from 0.1% by weight to 3% by weight with respect to the total weight of the catalytic composition.

12. The process according to claim 1, wherein said catalytic composition comprises tin, tin oxide, or both in an amount of from 0.001% by weight to 1% by weight with respect to the total weight of the catalytic composition.

13. The process according to claim 12, wherein said catalytic composition comprises tin, tin oxide, or both in an amount of from 0.05% by weight to 0.4% by weight with respect to the total weight of the catalytic composition.

14. The process according to claim 1, wherein said catalytic composition comprises platinum, platinum oxide, or both in an amount of from 1 to 99 ppm by weight with respect to the total weight of the catalytic composition.

15. The process according to claim 14, wherein said catalytic composition comprises platinum, platinum oxide, or both in an amount of from 1 to 50 ppm by weight with respect to the total weight of the catalytic composition.

16. The process according to claim 1, wherein the microspheroidal alumina has a surface area less than or equal to 150 $m_2/g$.

17. The process according claim 1, wherein said catalytic composition comprises silica in an amount of from 0.05% by weight to 5% by weight.

18. The process according to claim 1, wherein a remaining part of the catalytic composition, which is not sent to the regenerator, is recycled directly to the dehydrogenation section.

19. The process according to claim 1, wherein the dehydrogenating is conducted at a temperature of from 450° C. to 700° C.

20. The process according to claim 1, wherein the inert product and the reagents are in a volumetric ratio of from 1 to 9.

21. The process according to claim 1, wherein the dehydrogenating is conducted at a pressure of from 0.2 atm absolute to 2 atm.

22. The process according claim 1, wherein the inert product is selected from the group consisting of nitrogen, nitrogen mixed with methane, methane, and methane in the presence of hydrogen.

\* \* \* \* \*